(12) United States Patent
Townsend et al.

(10) Patent No.: US 6,413,232 B1
(45) Date of Patent: Jul. 2, 2002

(54) ORTHOPEDIC KNEE BRACE HAVING AN ADJUSTABLE KNEE PAD SUPPORT

(75) Inventors: Jeffrey Townsend; Steve Knecht, both of Bakersfield, CA (US)

(73) Assignee: Townsend Design, Bakersfield, CA (US)

( * ) Notice: Subject to any disclaimer, the term of this patent is extended or adjusted under 35 U.S.C. 154(b) by 3 days.

(21) Appl. No.: 09/593,606

(22) Filed: Jun. 12, 2000

(51) Int. Cl.[7] .................................................. A61F 5/00
(52) U.S. Cl. .......................................... 602/16; 602/26
(58) Field of Search .............................. 602/23, 5, 26, 602/16; 128/846, 882

(56) References Cited

U.S. PATENT DOCUMENTS

| | | | |
|---|---|---|---|
| 4,620,532 A | * 11/1986 | Houswerth | 602/16 |
| 4,846,842 A | * 7/1989 | Connolly | 602/26 |
| 4,940,045 A | 7/1990 | Cromartie | |
| 5,259,832 A | 11/1993 | Townsend et al. | |
| 5,807,294 A | 9/1998 | Cawley et al. | |
| 5,976,063 A | * 11/1999 | Joutras | 482/115 |

* cited by examiner

Primary Examiner—Michael A. Brown
(74) Attorney, Agent, or Firm—Nixon Peabody LLP; David S. Safran

(57) ABSTRACT

An orthopedic knee brace has a pair of femoral and tibial links, a hinge mechanism connecting the femoral and tibial links, a condylar knee pad support fixedly positioned on the lateral side of the brace and made adjustable by a spring-loaded ratchet mechanism featuring a series of interlocking teeth that allows for the axial displacement of the condylar pad to supply corrective force to the lateral knee joint and prevent of any unintended change in correction force. Moreover, in an effort to provide greater flexibility to the wearer in and enhance the stabilization of the design, the condylar pad is mounted for rotation about a point on the axis of the femoral condyle of the knee joint. The knee pad support may be adjusted by hand by rotating the ratchet mechanism to achieve the proper correction force or with an adjusting tool that engages a plurality of notches surrounding the periphery of the ratchet mechanism.

13 Claims, 3 Drawing Sheets

ORTHOPEDIC KNEE BRACE HAVING AN ADJUSTABLE KNEE PAD SUPPORT

BACKGROUND OF THE INVENTION

1. Field of the Invention

The present invention relates generally to orthopedic devices for the stabilization and control of a human knee joint that has been injured. More particularly, the invention relates to an orthopedic knee brace having an adjustable knee pad support that enables a wearer or medical professional to quickly and efficiently adjust the lateral corrective force placed on the knee joint by the support, thereby permitting control of the joint so as to optimize healing and stability.

2. Description of the Related Art

Orthopedic knee braces are commonly worn by patients after surgery for treatment of an injury to the knee joint. Knee braces generally serve dual purposes: first, the brace stabilizes the joint in order to control its lateral movement. Second, they limit joint flexion and/or extension in an adjustable and controllable manner to prevent recurrence of injury to the knee.

A knee brace of the initially mentioned type is disclosed in one of the present inventors U.S. Pat. No. 5,259,832, which discloses a multiaxis controlled knee brace utilizing a four bar joint mechanism and lateral and medial support pads for maintaining proper position of the knee brace when worn by the wearer. However, this design fails to provide for the independent adjustment of the support pads relative to the knee joint for providing stability to the knee joint. The use of orthopedic knee braces having adjustable support members is conventional within the prior art. Such an arrangement provides the knee brace with medial and/or lateral support pads that are positioned proximate to and in engagement with the medial and lateral sides of the knee joint to provide comfort and support to the wearer by stabilizing the knee joint against lateral movement.

The effectiveness of providing lateral stabilization to the knee joint is largely dependent upon the position of the pad. Incorrect or poor positioning of the knee brace, in particular the support pad, could result in the exacerbation of the existing knee injury by destabilizing the knee joint. Consequently, there have been many attempts to solve this problem by providing the knee brace with means for adjusting the lateral position of the support pads independent of the knee brace. However, certain shortcomings have been encountered with regard to the use of the conventional knee brace designs.

For example, U.S. Pat. No. 5,807,294 to Cawley et al. discloses a lateral support assembly for an osteoarthritic knee brace that utilizes an adjustable screw design to laterally adjust the position of a condylar pad member relative the knee joint. However, this design provides for adjusting the pad by using a tool to rotatably adjust the screw members, which requires that the tool be readily available to the wearer during times in which he or she must readjust the setting of the pad assembly and the need to separately adjust two screws complicates the adjustment process. In addition, in cases where the wearer flexed and extended their leg, the screws continued to independently adjust the support pad.

U.S. Pat. No. 4,940,045 to Cromartie discloses an adjustable medial condylar support pad affixed to a plate hingedly connected to an upper longitudinal rib within a medial side member of a knee brace. The support pad is manually adjusted by rotating a spacer member about a pivot point located above the support pad. While this device allows for the hand-held adjustment of the support pad, it does not provide for ease in adjustment since the spacer member is awkwardly positioned between the support pad and longitudinal rib. Furthermore, the hinge arrangement causes the support pad to be increasingly inclined relative to the knee joint as it is adjusted inward.

Accordingly, there is still a need for a lateral support device for an orthopedic knee brace that allows for simple and effective adjustment of the support pad in correcting the lateral force of the support pad on the knee joint. There also is a need for a support device that allows the wearer to quickly and easily adjust the device by hand when the knee brace is not fitted on the his or her leg.

SUMMARY OF THE INVENTION

In view of the foregoing, it is an object of the present invention to provide a lateral support device for an orthopedic knee brace that can be quickly adjusted to obtain the optimum degree of corrective force on the knee joint.

It is a further object of the present invention to provide a lateral support device for an orthopedic knee brace that will prevent any potential change in correction once it has been set. These and other objects and characteristics of the present invention are achieved in accordance with a preferred embodiment, which provides an orthopedic knee brace having a pair of femoral and tibial links and a hinge mechanism by which lateral side and medial side femoral links are pivotally connected to lateral side and medial side tibial links respectively. The knee brace also includes an adjustable knee pad support fixedly positioned on the lateral and medial sides of the knee joint, and a spring-loaded ratchet mechanism featuring a series of interlocking teeth that allows for the horizontal displacement of the pad support. This spring loaded design is an advantageous feature since it prevents any unintended change in correction force supplied by the pad supports. Moreover, in an effort to provide greater flexibility to the wearer in and enhance the stabilization of the design, the knee brace is designed such that the pad supports are mounted for rotation about a point on the axis of the femoral condyle of the knee joint. The knee pad support may be adjusted by hand by merely rotating the ratchet mechanism to achieve the proper correction or with an adjusting tool that engages a plurality of notches surrounding the periphery of the ratchet mechanism. During adjustment of the condylar pad, there is an audible click as the teeth engage in each subsequent position. The audible clicks enable it to be known how far the condylar pad has been laterally displaced toward the knee joint in an effort to increase the corrective force placed on the joint. In the fully extended setting, the condylar pad may extend for distances up to 3/16 of an inch from its original setting. The adjustability feature enables the wearer or medical professional to increase correction at least by an additional 1 to 5 degrees beyond the natural correction built into the knee brace. To decrease the corrective force, the ratchet mechanism is rotated past the last set of teeth and the condylar pad will be biased back to its original position by the spring.

These and other objects, features and advantages of the present invention will become more apparent from the following description when taken in conjunction with the detailed drawings which show, for purposes of illustration only, a single preferred embodiment of the present invention.

BRIEF DESCRIPTION OF THE DRAWINGS

The invention is described through a preferred embodiment illustrated in the accompanying drawings in which corresponding elements are labeled with the same reference numerals, in which.

DETAILED DESCRIPTION OF THE PREFERRED EMBODIMENT

Figure 1:
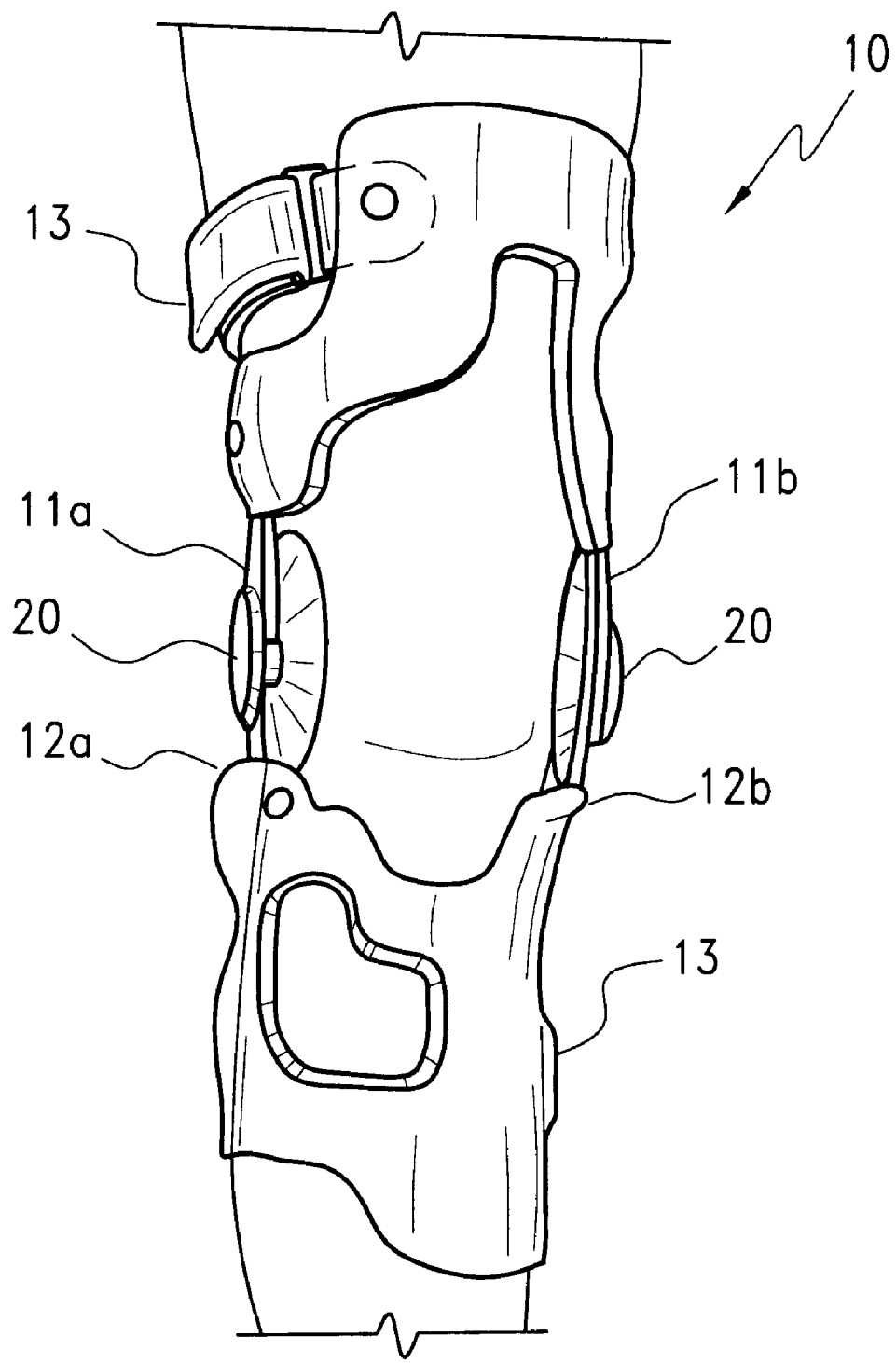
FIG. 1 is a perspective view of an orthopedic knee brace in accordance with a preferred embodiment of the invention.

Referring to the drawings, the orthopedic knee brace 10 of the present invention is best illustrated in FIG. 1. The brace comprises a pair of femoral links 11a, 11b and a pair of tibial links 12a, 12b which are in the form of a pair of upper struts and a pair of lower struts which can be formed of aluminum, titanium, or fiber and resin composites. A cuff and/or straps 13, of a known design, are provided for holding the knee brace 10 on the leg of a person requiring knee support.

The lateral (outer) side femoral link 11a is interconnected to the lateral side tibial link 12a via a hinge mechanism 20 and the medial (inner) side femoral link 11b is connected to the medial side tibial link 12b via a similar hinge mechanism 20. While the hinge mechanism 20 of the illustrated embodiment comprises a four bar joint mechanism that allows the knee joint to undergo a full range of motion during extension or flexion of the leg, the invention is not limited to the use of such a hinge. A fully adjustable knee pad support comprising a generally circular shaped condylar pad 1, 2 is designed to cover a pad holder 6 via a generally circular attachment device 3 and is configured to rest comfortably on the lateral and medial sides of the knee joint for maintaining proper positioning of the knee brace 10 and for stabilizing the knee joint. The design of the pad 1, 2 allows for quick and easy positioning of the knee brace 10 on the leg of the wearer. In particular, by partially flexing the knee (for example, approximately 25 to 35 degrees), the femoral condyle can be felt as a knob at the medial side of the knee joint and pad 1 can be placed on the femoral condyle as a way of properly locating the hinge mechanism 20 so that they it be centered relative to the horizontal axis passing through the femoral condyle. Consequently, the condylar pad 1, 2 on the medial and lateral knee joint can remain essentially stationary relative to the knee joint during flexion and extension of the leg, thereby avoiding any discomfort to the wearer due to rubbing of the pad 1, 2 against the side of the knee.

Figure 2:
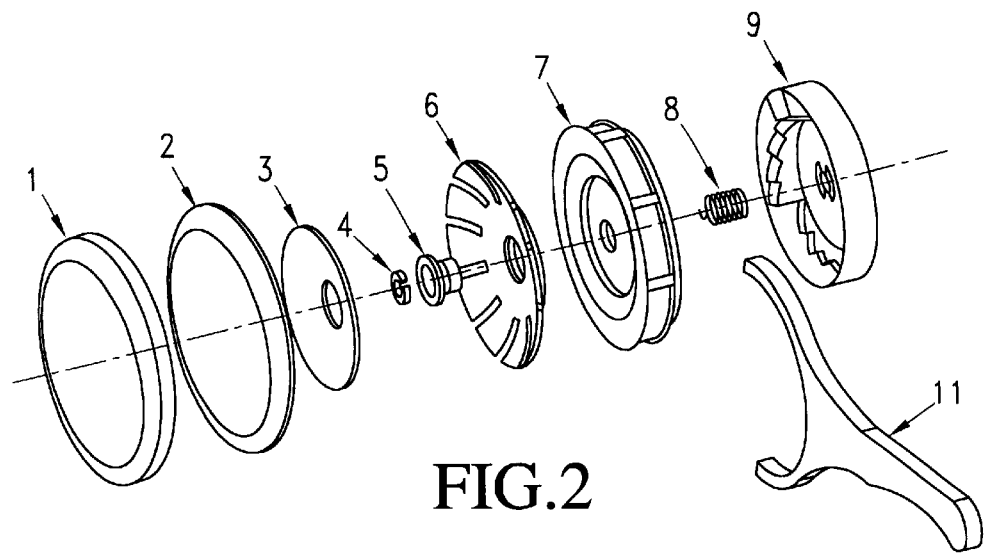
FIG. 2 is an exploded view of the knee pad support in accordance with a preferred embodiment of the invention.

As illustrated in FIG. 2, the adjustment of the condylar pad 1, 2 toward the side of the knee joint is accomplished using a ratchet mechanism 40. The ratchet mechanism 40 comprises a generally circular first adjustment member 9 having an annular set of inclined teeth 9a mounted about its inner periphery and a generally circular second adjustment member 7 that moves in a rotational direction about the first adjustment member 9 and also has an annular set of inclined teeth 7a mounted about its inner periphery for interlocking engagement with the first set of inclined teeth 9a. While an exemplary embodiment of the invention utilizes four sets of teeth having five individual teeth per set, any number of sets and individual teeth could be used in order to accomplish the task of displacing the second adjustment member 7 relative the first adjustment member 9. For example, an increased number of smaller individual teeth could result in enhanced adjustability of the knee pad support.

Adjustment of the condylar pad 1, 2 takes place by rotating the second adjustment member 7 relative to the first adjustment member 9, such rotation consequently imparting unidirectional motion to the second adjustment member 7 to displace the pad 1, 2 horizontally. In addition, the adjustment feature of the preferred embodiment is designed such that the second adjustment member 7 is axially displaceable from an original setting in which it rests on the first adjustment member 9 at a reference point zero to at least four incremental settings that increase in length to a maximum displacement distance of approximately 3/16 of an inch. For purposes of ease in manufacturing and costs, each of the first adjustment member 9 and second adjustment member 7 and their respective inclined teeth 7a, 9a are fabricated of a one-piece molded plastic material.

Figure 3:
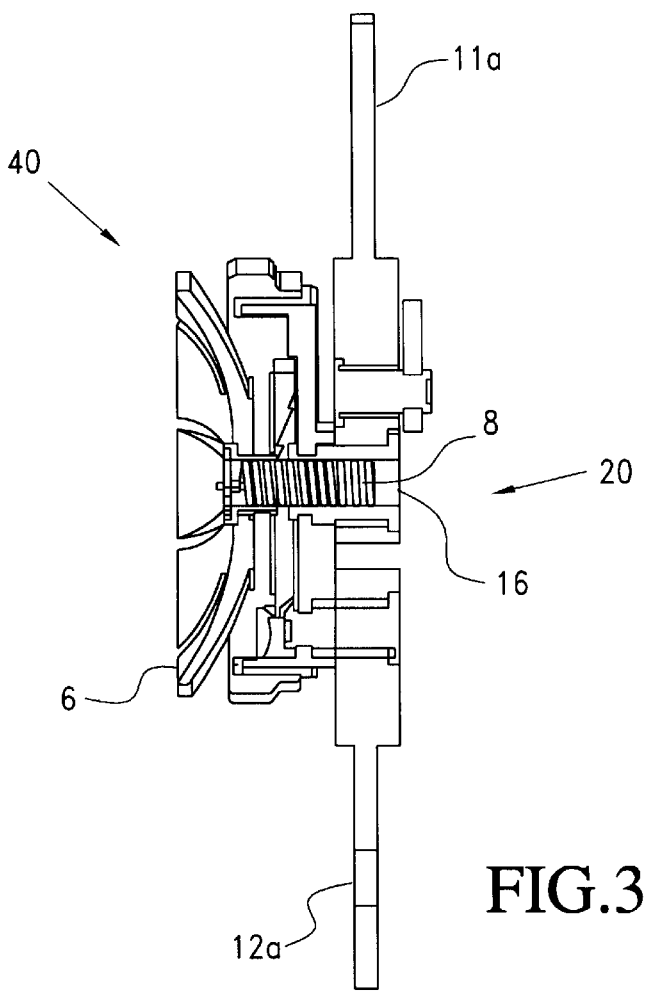
FIG. 3 is a cross-sectional view of the knee pad support in accordance with a preferred embodiment of the invention.

FIG. 3 shows a sectional view of the knee support pad that best exemplifies the spring action feature of the ratchet mechanism 40. Spring member 8 includes a coil spring having a circular attachment loop at its upper projectory end where it is axially positioned through the first 9 and second 7 adjustment members and secured to the knee brace 10 at its lower end by a set screw 16. The attachment loop extends through a rivet 5 located at the top surface of the pad holder 6 where it is held by a fastening device such as a spring retainer 4 extending through the loop at the projectory end of the spring member 8. The spring member 8 acts to pull the second adjustment member 7 axially towards the first adjustment member 9 so that the selected setting force is maintained, thereby preventing the unintentional movement of the second adjustment member 7 to a different setting.

Figure 4:
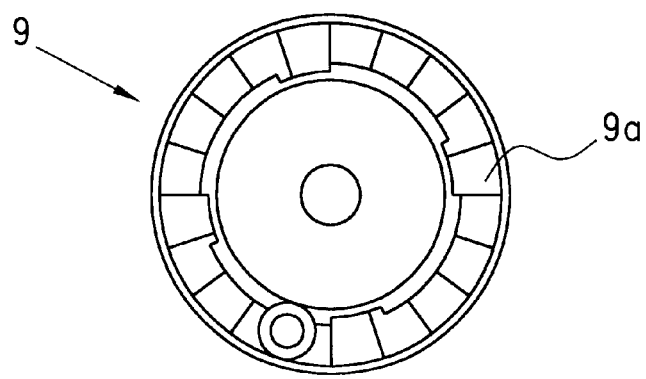
FIG. 4 is a top view of an adjustment member in accordance with a preferred embodiment of the invention.
Figure 5:
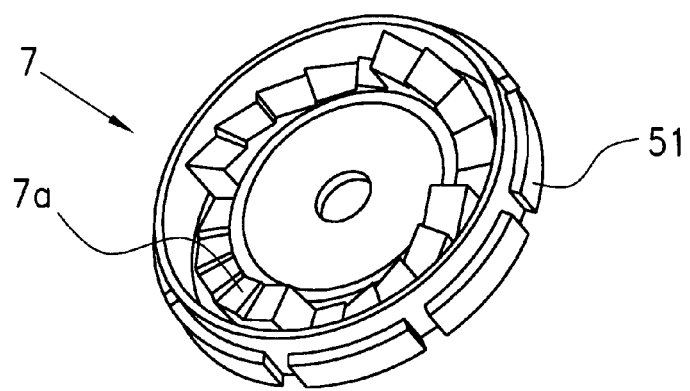
FIG. 5 is a planar view of an adjustment member in accordance with a preferred embodiment of the invention.

FIGS. 4 and 5 best illustrate the interlocking ratchet teeth 7a, 9a used to displace the second adjustment member 7 axially away from the first adjustment member 9 and towards the side of the knee joint to increase the correctional force by the condylar pad 1, 2 on the joint. The teeth 7a, 9a are designed for unidirectional rotation of the second adjustment member 7 to axially displace the second adjustment member 7, thereby moving the condylar pad 1, 2 in a horizontal direction towards the knee joint.

During operation, the condylar pad 1,2 maybe effortlessly and quickly adjusted by hand by rotating the ratchet mechanism 40 counterclockwise until the proper correction force is placed upon the joint. As the correction force is increased, there is an audible click as the teeth 7a, 9a engage in the next position, horizontally displacing the condylar pad 1, 2 further toward the knee joint. In the fully extended setting, the condylar pad 1, 2 will be displaced inward at least 3/16 of an inch from its original position. To decrease correction, the ratchet mechanism 40 is rotated past the last set of teeth 7a, 9a at which point the condylar pad 1, 2 will be returned to its original position by the spring member 8 located within the ratchet mechanism 40. This adjustability feature enables the wearer or medical professional to increase correction at least by an additional 1 to 5 degrees beyond the correction built into the knee brace and to easily reset the support if necessary.

The design of the hand adjustment obviates the need for any outside tools or other adjustment devices that result in complicated and time-consuming adjustment. However the ratchet mechanism 40 may be constructed to also be operable with a hand-held adjusting tool 11 that clips onto notches 51 surrounding the periphery of the ratchet mechanism 40. Adjustment of the settings of condylar pad 1, 2 by the ratchet mechanism 40 occurs in the same manner as by hand, but use of the tool 11 can make adjustment easier when the knee brace 10 is on the wearer.

While the present invention has been illustrated and described in connection with what is considered the most practical and preferred embodiment, it is understood that this invention is not limited to the embodiment disclosed herein but is intended to cover various arrangements included within the spirit and scope of the broadest interpretations and equivalent arrangements.

What is claimed is:

1. An orthopedic knee brace for controlling movement of the femur relative to the tibia during extension and flexion of a wearer's leg, said brace comprising:
    a pair of femoral links;
    a pair of tibial links;
    a hinge mechanism linking each of said of femoral links to a respective one of said pair of tibial links;
    a pad configured for fitting on the knee joint of the wearer; and
    a pad support adjustably mounted to at least one of said hinge mechanisms for displacing the pad in a laterally inward direction relative to the hinge mechanism, said pad support including:
        a first adjustment member mounted to a laterally inner side of said hinge mechanism; and
        a second adjustment member mounted adjacent said first adjustment member so as to be laterally inwardly displaceable relative to said first adjustment member.

2. An orthopedic knee brace as recited in claim 1, wherein a ratchet mechanism is provided for displacing said second adjustment member relative to said first adjustment member.

3. An orthopedic knee brace as recited in claim 2, wherein said ratchet mechanism includes at least one first set of inclined teeth annularly mounted about an inner periphery of said first adjustment member and at least one second set of inclined teeth annularly mounted about an inner periphery of said second adjustment member, said first set of inclined teeth being in interlocking engagement with said first set of inclined teeth.

4. An orthopedic knee brace as recited in claim 3, wherein there are four sets of first and second inclined teeth.

5. An orthopedic knee brace as recited in claim 4, wherein each set of inclined teeth includes at least five teeth.

6. An orthopedic knee brace as recited in claim 2, wherein said second adjustment member is displaceable relative to said first adjustment member by a maximum of about 3/16 of an inch.

7. An orthopedic knee brace as recited in claim 3, wherein said first adjustment member and said at least one first set of inclined teeth are composed of one-piece of molded plastic, and wherein said second adjustment member and said at least one second set of inclined teeth are composed of one-piece of molded plastic.

8. An orthopedic knee brace as recited in claim 1, wherein said second adjustment member has a plurality of tool-engageable notches surrounding its outer periphery.

9. An orthopedic knee brace as recited in claim 8, further comprising a hand tool for laterally inwardly displacing said second adjustment member relative to said first adjustment member, said hand tool having a first portion for engaging said notches and a hand-grippable second portion for applying a torque to said second adjustment member.

10. An orthopedic knee brace as recited in claim 1, wherein said hinge mechanism is a four bar joint mechanism.

11. An orthopedic knee brace as recited in claim 1, wherein said second adjustment member is mounted for rotation relative to said first adjustment member about a point aligned with the femoral condyle of a wearer's knee joint while in use.

12. An orthopedic knee brace as recited in claim 1, further comprising means for tensioning said second adjustment member against said first adjustment member.

13. An orthopedic knee brace as recited in claim 12, wherein said means for tensioning comprises a spring extending through said adjustment members.

* * * * *